United States Patent [19]
Samson et al.

[11] Patent Number: 5,334,154
[45] Date of Patent: Aug. 2, 1994

[54] PERFUSION TYPE DILATATION CATHETER HAVING PERFUSION PORTS WITH DEPRESSED PROXIMAL EDGES

[75] Inventors: Wilfred J. Samson, Saratoga; Motasim M. Sirhan, Santa Clara; Jovito L. Fernando, Modesto, all of Calif.

[73] Assignee: Advanced Cardiovascular Systems, Inc., Santa Clara, Calif.

[21] Appl. No.: 925,568

[22] Filed: Aug. 4, 1992

[51] Int. Cl.$^5$ ............................................. A61M 29/00
[52] U.S. Cl. ..................................... 604/102; 604/96; 604/280; 606/194
[58] Field of Search ................... 606/192, 194; 604/96, 604/102, 280

[56] References Cited

U.S. PATENT DOCUMENTS

| | | | |
|---|---|---|---|
| 4,784,638 | 11/1988 | Ghajor et al. | 604/49 |
| 4,877,031 | 10/1989 | Conway et al. | 606/194 |
| 4,892,519 | 1/1990 | Songer et al. | 604/96 |
| 5,021,044 | 6/1991 | Sharkawy | 604/53 |
| 5,046,503 | 9/1991 | Schneiderman | 128/692 |
| 5,087,247 | 2/1992 | Horn et al. | 604/98 |
| 5,160,321 | 11/1992 | Sahota | 604/96 |
| 5,180,364 | 1/1993 | Ginsberg | 604/53 |

Primary Examiner—C. Fred Rosenbaum
Assistant Examiner—Corrine Maglione

[57] ABSTRACT

A perfusion-type dilatation catheter with perfusion ports in the wall of the catheter shaft wherein the proximal edges of the perfusion ports have depressions extending into a guidewire receiving inner lumen which passes through the catheter shaft. The depressed proximal edges prevent excursions of guidewires through the perfusion ports as the guidewire is passed through the guidewire receiving inner lumen. The perfusion ports may be conveniently made by forming holes into the wall of the catheter shaft, inserting shaping pins into the holes, heating the wall of the catheter shaft to make it readily deformable and then rotating the shaping pins proximally along the longitudinal axis of the catheter shaft so that the rotated shaping pins form depressions along the proximal edges of the perfusion ports which extend into the guidewire receiving inner lumen within the catheter shaft.

10 Claims, 2 Drawing Sheets

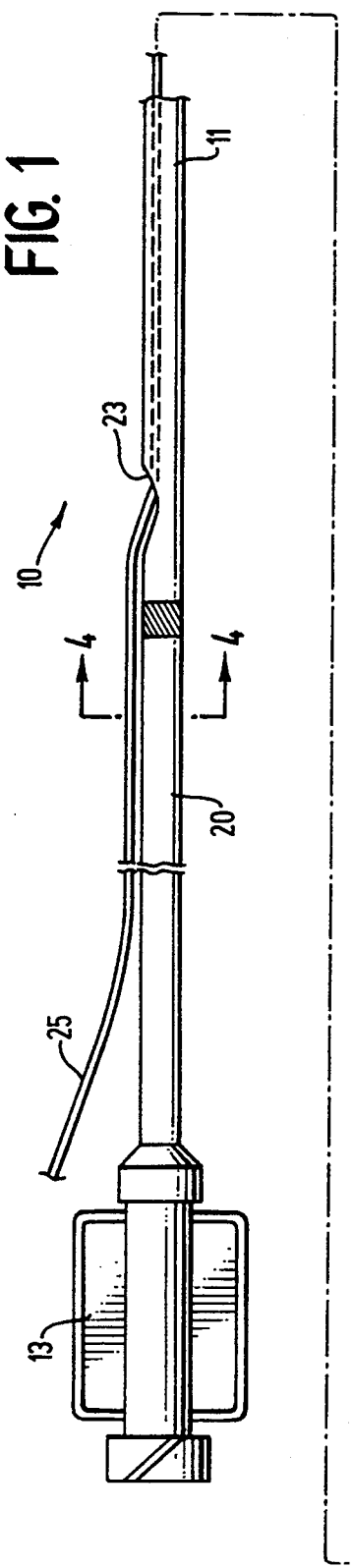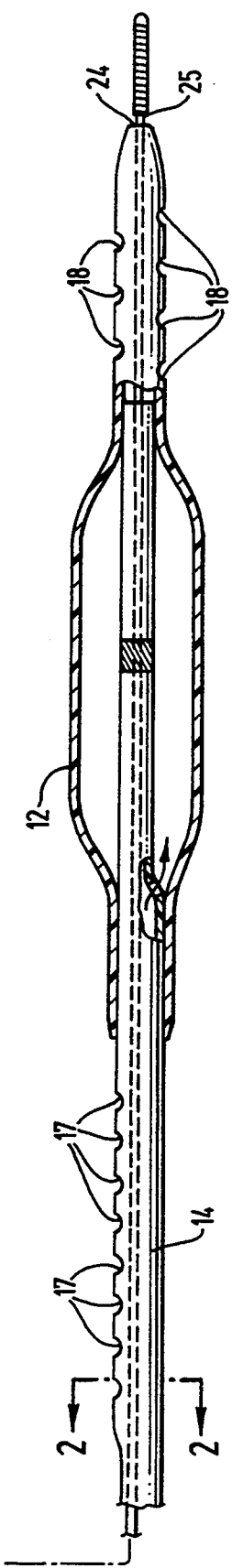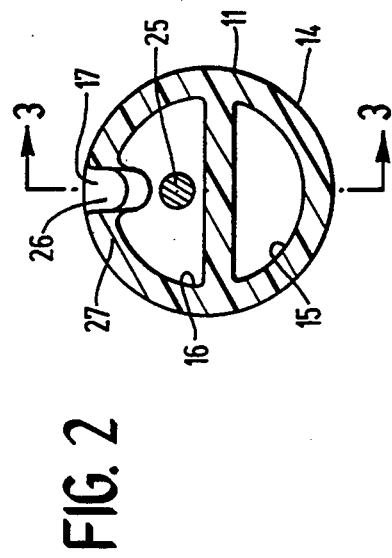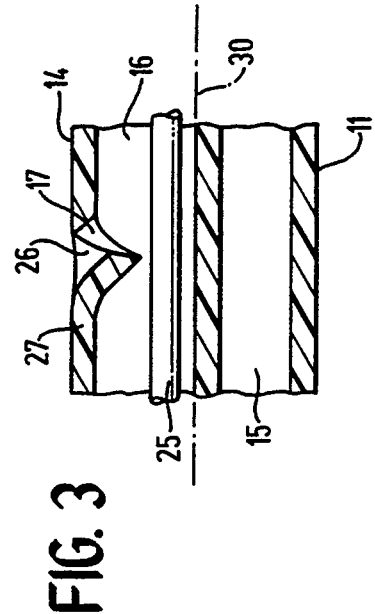

PERFUSION TYPE DILATATION CATHETER HAVING PERFUSION PORTS WITH DEPRESSED PROXIMAL EDGES

BACKGROUND OF THE INVENTION

This invention generally relates to perfusion-type balloon dilatation catheters used in percutaneous transluminal coronary angioplasty (PTCA).

PTCA is a widely used procedure for the treatment of coronary heart disease. In this procedure, a balloon dilatation catheter is advanced into the patient's coronary artery and the balloon on the catheter is inflated within the stenotic region of the patient's artery to open up the arterial passageway and increase the flow of blood through the artery. To facilitate the advancement of the dilatation catheter into the patient's coronary artery, a guiding catheter having a preshaped distal tip is first percutaneously introduced into the cardiovascular system of a patient by the Seldinger technique through the brachial or femoral arteries. The catheter is advanced until the preshaped distal tip of the guiding catheter is disposed within the aorta adjacent the ostium of the desired coronary artery. The guiding catheter is twisted or torqued from the proximal end, which extends out of the patient, to guide the distal tip of the guiding catheter into the ostium. A balloon dilatation catheter may then be advanced through the guiding catheter into the patient's coronary artery until the balloon on the catheter is disposed within the stenotic region of the patient's artery where it is inflated to open up the arterial passageway.

The perfusion-type dilatation catheter for angioplasty was introduced into the marketplace by Advanced Cardiovascular Systems, Inc.(ACS). This catheter, which can take the form of an over-the-wire, a fixed-wire or a rapid exchange type catheter, has one or more perfusion ports proximal and one or more perfusion ports distal to the dilatation balloon which are in fluid communication with a guidewire receiving inner lumen extending to the distal end of the catheter. When the balloon is inflated to dilate a stenosis, oxygenated blood in the artery or the aorta, or both, depending upon the location of the dilatation catheter within the coronary anatomy, is forced to pass through the proximal perfusion ports, through the inner lumen of the catheter and out the distal perfusion ports. The catheter provides oxygenated blood downstream from the inflated balloon which in turn prevents or minimizes ischemic conditions in tissue distal to the catheter. The perfusion of blood distal to the inflated balloon allows for long term dilatations, e.g. 30 minutes or even several hours or more. Commercially available perfusion-type dilatation catheters, which have been highly praised by the medical profession and which have met with much commercial success, include the STACK PERFUSION® Dilatation Catheter which is sold by ACS.

When using an over-the-wire version of a perfusion-type dilatation catheter, a guidewire is usually inserted into an inner lumen of the dilatation catheter before it is introduced into the patient's vascular system and then both are introduced into and advanced through the guiding catheter to its distal tip seated within the ostium of the desired coronary artery. The guidewire is first advanced out of the seated distal tip of the guiding catheter into the desired coronary artery until the distal end of the guidewire extends beyond the lesion which is to be dilatated. The dilatation catheter is then advanced out of the distal tip of the guiding catheter into the patient's coronary artery, over the previously advanced guidewire, until the balloon on the distal extremity of the dilatation catheter is properly positioned across the lesion to be dilatated. Once properly positioned across the stenosis, the balloon is inflated to a predetermined size with radiopaque liquid at relatively high pressures (e.g., generally 4–12 atmospheres), usually for extended periods, to dilate the stenosed region of a diseased artery. After the inflation, the balloon is finally deflated so that the dilatation catheter can be removed from the dilated stenosis to resume blood flow.

The rapid exchange version of the perfusion-type dilatation catheter has a short guidewire receiving sleeve or inner lumen extending through a distal portion of the catheter. The sleeve or inner lumen extends proximally from a first guidewire port in the distal end of the catheter to a second guidewire port in the catheter spaced proximally from the inflatable member of the catheter. Perfusion ports are provided proximal and distal to the inflatable member or balloon which are in fluid communication with the short guidewire receiving sleeve or inner lumen. A slit may be provided in the wall of the catheter body which extends distally from the second guidewire port, preferably to a location proximal to the location of the balloon. The structure of the catheter allows for the rapid exchange of the catheter without the need for an exchange wire or adding a guidewire extension to the proximal end of the guidewire.

The rapid exchange type perfusion catheter was introduced by ACS under the trademark the ACS RX PERFUSION® Coronary Dilatation Catheter. This catheter has likewise been widely praised by the medical profession and it has met with much success in the marketplace because of the advantages of its unique design. The rapid exchange features of this catheter are described and claimed in U.S. Pat. No. 5,040,548 (Yock), U.S. Pat. No. 5,061,273 (Yock) and U.S. Pat. No. 4,748,982 (Horzewski et al.) which are incorporated herein by reference.

One of the problems encountered with perfusion-type catheters is that when a guidewire is advanced within the guidewire lumen of the catheter, the guidewire may occasionally pass through a perfusion-port in the catheter shaft. This has become more common as the guidewire diameters have become smaller. Such guidewire excursions through the perfusion ports are not desireable because they interfere with the angioplasty procedure. In such a case the guidewire has to be withdrawn proximally to disengage the guidewire from the perfusion port and then advanced through the catheter lumen. If the guidewire excursion deformed the distal tip of the guidewire, the guidewire may have to be completely withdrawn from the patient so that the distal tip can be reshaped and then readvanced through the catheter shaft. When a guidewire passes out one of the perfusion ports, it may traumatically engage the blood vessel wall. Additionally, as catheter profiles are reduced, the more difficult it is to provided adequate blood flow distal to the balloon to avoid ischemic conditions. What has been needed and previously unavailable is an easily manufactured perfusion-type catheter which will reduce the incidence of a guidewire passing through a perfusion port when the guidewire is advanced through the guidewire lumen and provide effective blood flow through the perfusion ports to ensure adequate blood flow distal to the balloon when the balloon is inflated. The present invention satisfies these and other needs.

SUMMARY OF THE INVENTION

The present invention is directed to a perfusion-type intravascular catheter which precludes the excursion of a guidewire through a perfusion port of the catheter when the guidewire is advanced through an guidewire lumen of the catheter which is in fluid communication with the perfusion ports.

The perfusion-type intravascular catheter of the invention has one or more perfusion ports which extend through the wall of the catheter shaft and which have inwardly depressed proximal edges. The depressed proximal edges prevent the excursion of a guidewire through the perfusion ports when the guidewires are advanced through the catheter shaft. In one presently preferred embodiment the proximal edge has a scoop-like structure which is inclined inwardly in the distal direction.

The above described perfusion ports can be formed in the catheter shaft wall by first forming a plurality of holes through the catheter shaft wall by suitable means such as mechanical drilling or laser beam, inserting shaping pins having a diameter about the size of the diameter of the holes in the catheter shaft wall, heating the catheter shaft wall and rotating the shaping pins in the proximal direction along the longitudinal axis of the catheter shaft while the catheter shaft wall is at an elevated temperature to form the scoop-like depressed proximal edges of the perfusion ports. This procedure will also form a scoop-shaped rise on the exterior of the catheter shaft at the distal edge of the perfusion port, which is not very desirable because the outwardly extending scoop-shaped deformation can traumatically engage the artery wall upon the removal of the catheter. To eliminate these upwardly projecting scoop-like deformations in the catheter shaft, it is preferred to withdraw the shaping pins and to apply pressure to the exterior of the catheter shaft wall around the distal edge of the holes while the material is at elevated temperature to reform the distal edge into the same contour as the surrounding exterior of the catheter shaft. The desired pressure can be conveniently applied to the distal edge of the perfusion port by heat shrinking a sheath tightly about the holes after the pins have been removed.

The perfusion ports of the invention prevent the excursion of a guidewire therethrough and also facilitate the flow of blood through the perfusion ports. These and other advantages of the invention will become more apparent from the following detailed description of the invention when taken in conjunction with the accompanying exemplary drawings.

BRIEF DESCRIPTION OF THE DRAWINGS

FIG. 1 is an elevational view, partially in section, of a perfusion-type dilatation catheter embodying features of the invention.

FIG. 2 is a transverse cross-sectional view of the catheter shown in FIG. 1 taken along the lines 2—2.

FIG. 3 is a partial longitudinal view in section of the catheter shown in FIG. 1 taken through one of the perfusion ports.

DETAILED DESCRIPTION OF THE INVENTION

Figure 4:
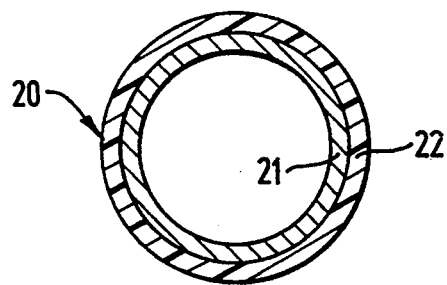
FIG. 4 is a transverse cross-sectional view of the catheter shown in FIG. 1 taken along the lines 4—4.

FIGS. 1-4 illustrate a rapid exchange version of a perfusion-type dilatation catheter 10 of the invention. The catheter 10 includes an elongated catheter shaft 11, an inflatable member 12 on the distal portion of the catheter shaft and an adapter 13 on the proximal end of the catheter shaft. The distal portion 14 of the catheter shaft, as best shown in FIG. 2 has two inner lumens, a first inflation lumen 15 and a guidewire receiving lumen 16 which extends parallel to the inflation lumen. A plurality of perfusion ports 17 are provided in the catheter shaft 11 proximal to the inflatable member 12 and a plurality of perfusion ports 18 are provided in the catheter shaft distal to the inflatable member. The proximal portion 20 of the catheter shaft 11, which is illustrated in FIG. 4, comprises a high strength tubular element 21, such as a stainless steel hypotube section, and a plastic jacket or coating 22. The guidewire receiving inner lumen 16 extends between proximal guidewire port 23 which is proximal to the proximal perfusion ports and distal guidewire port 24 which is located in the distal end of the catheter. Guidewire 25 is disposed within lumen 16.

The details of a proximal perfusion port 17 are depicted in FIGS. 2 and 3. As shown, the perfusion port 17 includes a scoop-like depression 26 formed in the wall 27 of the catheter shaft 11 at the proximal edge of the perfusion port which extends into the guidewire receiving inner lumen 16 and is generally inclined toward the distal end of the catheter. While the preferred depression 26 of the catheter shaft wall 27 is shown as being scoop-like, it may take other forms provided that it blocks access to the perfusion port when a guidewire 25 is advanced distally through the perfusion portion of the guidewire receiving inner lumen 16.

Figure 5:
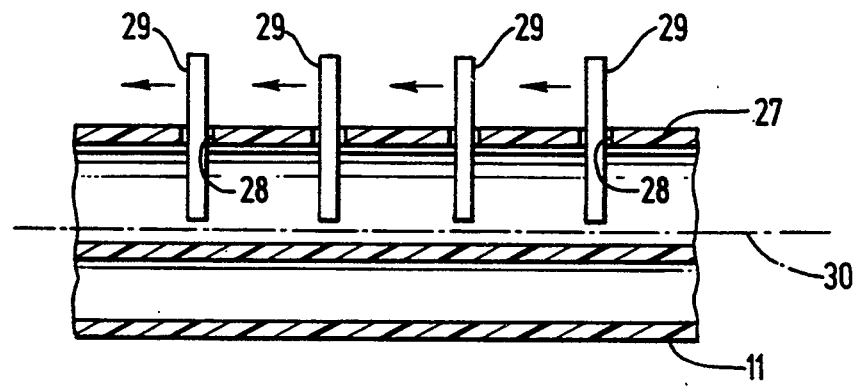
FIGS. 5-6 illustrate the process steps for forming the perfusion ports of the invention.
Figure 6:
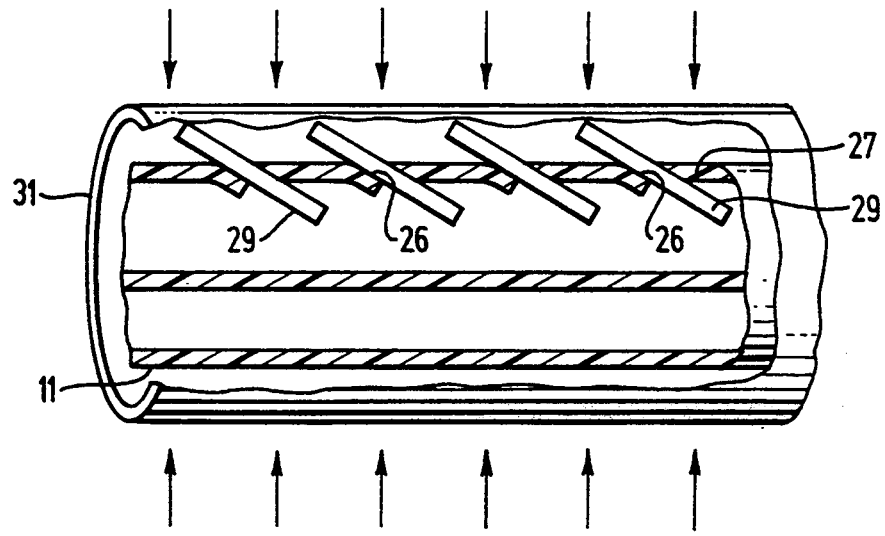

FIGS. 5-6 illustrate a method of forming the perfusion ports 17 and 18 previously discussed. Initially, the holes 28 are formed in the wall 27 of the catheter shaft 11 by suitable means such as by drilling or by use of a laser. Shaping pins 29 are placed into the holes 28 as shown in FIG. 5 and then rotated proximally along the longitudinal axis 30 of the catheter while a sheath 31 is disposed about the shaft 11. The catheter shaft 11, the pins 29 and the sheath 31 are heated to a temperature which softens the catheter wall 27. When heated, the sheath 31 heat shrinks against the rotated pins 29 and the shaft 11 so that the pins 29 heat form the softened proximal edges of the holes 28 into the scoop-like depressions 26. The pressure applied to the distal edges of the holes 28 by the shaping pins 29 raises the distal edges of the holes when the pins 29 are rotated. Perfusion ports having raised distal edges are not desireable because they can scrape the artery wall when the catheter 10 is withdrawn from the patient. To eliminate the raised distal edges, the sheath 31 and the shaping pins 29 are removed after forming the scoop-like depressions 26 and a second heat shrinkable sheath 32, much like the first sheath 31, is placed about the catheter shaft over the perfusion ports and then heat shrunk to heat form the distal edges of the perfusion ports into a less traumatic construction and preferably into essentially the same contour as the exterior of the catheter shaft.

The various components of the catheter of the present invention can be made from conventional materials. The distal portion 14 of the catheter shaft 11 can be extruded or otherwise formed from plastic resins such as polyethylene and polyesters (e.g., Hytrel) and the balloon 12 can be formed from polyethylene, polyethylene terephthalate or oleophillic ionomers such a sold under the trademark Surlyn ® by duPont, deNemours & Co. The core of the guidewire 25 may be made of stainless steel or superelastic NiTi alloys which exhibit a stress induced phase transformation at body temperature. The sheath can be formed of suitable heat shrinkable plastic material such as polyethylene.

For coronary angioplasty procedures, the outer diameter of the proximal portion 20 of catheter shaft 11 can typically range from about 0.035 to about 0.05 inch (0.89–1.30 mm) and the distal section 14 of the shaft can range from about 0.04 to about 0.06 inch (1.02–1.52 mm). The inflated diameters of the balloon 12 can range from about 1.0 to about 5 mm. The dimensions of the inflation lumen 15 are chosen to provide adequate times for inflation and deflation of the balloon. The dimensions of the guidewire receiving lumen 16 are chosen to allow for the slidable advancement of the guidewire through the lumen. The dimensions of inner lumen 16 between the most proximal and the most distal perfusion ports is sufficiently large to provide adequate blood flow through the catheter. The overall length of the catheter can range from about 130 to about 150 cm. For other intraluminal procedures the dimensions may be changed to better accommodate for the needs of the particular procedure.

While the present invention has been described herein in terms of certain presently preferred embodiments directed to dilatation catheters for coronary angioplasty, those skilled in the art will recognize that invention is suitable for other types of catheters used with guidewires. For example, the perfusion ports of the invention may be utilized with the "bail out" type perfusion catheters such as disclosed in U. S. Pat. No. 4,661,094 (Simpson). Various modifications and improvements can be made without departing from the scope of the invention.

What is claimed is:

1. A perfusion-type intravascular catheter comprising:
   a) an elongated shaft having proximal and distal portions and a guidewire receiving inner lumen extending through at least the distal portion of the shaft to a guidewire port in the distal end of the shaft; and
   b) at least one perfussion port which extends through a wall of the elongated shaft, which is in fluid communication with the guidewire receiving inner lumen of the shaft and which has a lower proximal edge which is inwardly depressed into the guidewire receiving inner lumen to prevent a guidewire from passing through the perfusion port when the guidewire is advanced distally through the guidewire receiving inner lumen.

2. The intravascular catheter of claim 1 wherein the inwardly depressed proximal edge of the perfusion port has a scoop-like shape.

3. The intravascular catheter of claim 1 wherein the inwardly depressed proximal edge of the perfusion port is inclined toward the distal end of the shaft.

4. The intravascular catheter of claim 1 wherein the perfusion port has a distal edge which has the same contour as the catheter shaft.

5. The intravascular catheter of claim 1 wherein an inflation lumen extends through the catheter shaft and an inflatable member is provided on the distal portion of the catheter shaft which is in fluid communication with the inflation lumen.

6. A perfusion-type dilatation catheter comprising:
   a) an elongated catheter shaft having proximal and distal ends, a guidewire receiving inner lumen extending through at least a distal portion of the shaft to a guidewire port in the distal end of the shaft and an inflation lumen extending from the proximal end of the shaft;
   b) an inflatable member on a distal portion of the catheter shaft having an interior in fluid communication with the inflation lumen extending from the proximal end of the catheter shaft; and
   c) at least one perfusion port extending through a wall of the elongated catheter shaft defining at least in part the guidewire receiving inner lumen of the shaft, the perfusion port having a lower proximal edge which is inwardly depressed into the guidewire receiving inner lumen to prevent a guidewire from passing through the perfusion port when being advanced distally through the guidewire receiving inner lumen.

7. The dilatation catheter of claim 6 including an adapter on the proximal end of the catheter shaft for directing inflation fluid from a source through the inflation lumen to the interior of the inflatable member.

8. The dilatation catheter of claim 6 wherein a plurality of perfusion ports having inwardly depressed proximal edges are provided in the catheter shaft proximal to the inflatable member.

9. The dilatation catheter of claim 8 wherein the guidewire receiving inner lumen extends within the distal portion of the catheter shaft between a proximal guidewire port located proximal to the perfusion ports in the catheter shaft proximal to the inflatable member and the distal guidewire port.

10. The dilatation catheter of claim 6 wherein a plurality of perfusion ports having inwardly depressed proximal edges are provided in the catheter shaft distal to the inflatable member.

* * * * *